United States Patent
Mizukami et al.

(10) Patent No.: US 7,459,920 B2
(45) Date of Patent: Dec. 2, 2008

(54) METHOD OF AND APPARATUS FOR NON-DESTRUCTIVELY MEASURING MOISTURE CONTENT OF DRIED OBJECTS

(75) Inventors: Yuzo Mizukami, Shizuoka (JP); Yuichi Yamaguchi, Shizuoka (JP); Yusuke Sawai, Shizuoka (JP)

(73) Assignee: Incorporated Adminstrative Agency National Agriculture and Food Research Organization, Tsukuba (JP)

( * ) Notice: Subject to any disclaimer, the term of this patent is extended or adjusted under 35 U.S.C. 154(b) by 0 days.

(21) Appl. No.: 11/660,744

(22) PCT Filed: Aug. 23, 2004

(86) PCT No.: PCT/JP2004/012063

§ 371 (c)(1),
(2), (4) Date: Feb. 22, 2007

(87) PCT Pub. No.: WO2006/021985

PCT Pub. Date: Mar. 2, 2006

(65) Prior Publication Data

US 2007/0241756 A1  Oct. 18, 2007

(51) Int. Cl.
*G01R 27/02* (2006.01)
(52) U.S. Cl. ............... 324/715; 324/444; 324/690; 324/694; 324/717; 426/231
(58) Field of Classification Search .......... 324/715; 460/7
See application file for complete search history.

(56) References Cited

U.S. PATENT DOCUMENTS 4,817,021 A * 3/1989 Sowerby et al. ......... 702/137
5,479,104 A * 12/1995 Cambell .................. 324/690
5,560,246 A * 10/1996 Bottinger et al. ........ 73/861.15

(Continued)

FOREIGN PATENT DOCUMENTS

JP  40-14479  5/1965

(Continued)

OTHER PUBLICATIONS

Hitoshi Yoshitomi et al, *Automatic Control of Tea Manufacturing Process* (Part 2), National Institute of Vegetable and Tea Science, 2002, pp. 101-108, Shizuoka, Japan, abstract only.

*Primary Examiner*—Vincent Q. Nguyen
*Assistant Examiner*—Benjamin M Baldridge
(74) *Attorney, Agent, or Firm*—Arent Fox LLP

(57) ABSTRACT

Methods and apparatuses for obtaining electrical characteristics and moisture content of dried objects having different shapes and sizes through impedance and electrostatic capacity measurements are provided. Measuring the moisture content of dried objects comprises the steps of: introducing dried objects of different sizes and shapes into a container, inserting four electrode terminals into the container, measuring electrical characteristics between two electrodes based on the dried objects and inputting measurement results into a high impedance voltmeter. An apparatus is provided comprising: a container for accommodating dried objects having different sizes and shapes, four electrode terminals inserted into the container, an AC signal having a predetermined voltage to be applied to the terminals, and a high impedance voltmeter for measuring and receiving electrical characteristics between two terminals based on the dried objects.

1 Claim, 4 Drawing Sheets

U.S. PATENT DOCUMENTS

| | | | | |
|---|---|---|---|---|
| 5,859,536 A | * | 1/1999 | Stockton | 324/664 |
| 2002/0060576 A1 | * | 5/2002 | Tominaga | 324/715 |
| 2002/0170548 A1 | * | 11/2002 | Masters et al. | 123/641 |
| 2003/0001595 A1 | * | 1/2003 | Steele et al. | 324/717 |
| 2004/0095154 A1 | * | 5/2004 | Lundstrom et al. | 324/694 |
| 2006/0188616 A1 | * | 8/2006 | Pierce et al. | 426/231 |

FOREIGN PATENT DOCUMENTS

| | | |
|---|---|---|
| JP | 59-23652 U | 2/1984 |
| JP | 2660288 B2 | 6/1997 |
| JP | 09-243683 A | 9/1997 |
| JP | 2003-294654 A | 10/2003 |

\* cited by examiner

RELATION BETWEEN A MOISTURE CONTENT CALCULATED FROM IMPEDANCE/ELECTROSTATIC CAPACITY MEASURED AT A FREQUENCY OF 3.0 KHz ON ONE HAND AND A MOISTURE CONTENT MEASURED BY A DRIED TYPE MEASURING METHOD ON THE OTHER

METHOD OF AND APPARATUS FOR NON-DESTRUCTIVELY MEASURING MOISTURE CONTENT OF DRIED OBJECTS

CROSS-REFERENCE TO RELATED APPLICATION

This application is a National Stage entry of International Application No. PCT/JP2004/1012063, filed Aug. 23, 2004, the entire specification claims and drawings of which are incorporated herewith by reference.

TECHNICAL FIELD

The present invention relates to a method of and an apparatus for measuring a moisture content of dried objects during a drying process for drying agricultural products, fruits, and marine products having different shapes and different characters, using their electrical properties without damaging the dried objects themselves.

BACKGROUND TECHNIQUE

Conventionally, there has been known a process of measuring a moisture content of tea leaves in accordance with a DC electric resistance in tea processing, but it has been found that there is almost no correlation between a moisture content and a DC electric resistance (for example, see the following non-patent document 1). Further, the following patent document 1 entitled "method of and apparatus for determining a tea leave taking-out timing during a tea processing" shows that tea leaves may be placed between electrodes, and a direct current is caused to flow between the electrodes so as to measure an electric resistance between the electrodes, thereby determining an appropriate timing for taking out the tea leaves from a rough rubbing machine. This, however, causes a problem that there is an irregularity in measured values due to different states of tea leaves and different states of electrodes. Further, there has been known a method of using a micro wave to measure a moisture content of tea leaves during tea leave processing tea leaf processing, but since it is necessary to at first measure a specific gravity of tea leaves and then measure a moisture content thereof in accordance with an attenuation of micro wave, an apparatus for use in such a measurement is quite complicated (for example, see the following patent document 2). As a result, judging an actual dried state of tea leaves usually depends upon a human operator's sense.

Patent Document 1; Japanese Patent Gazette No. 2660288
Patent Document 2; Japanese Unexamined Patent Application Publication No. 2003-294654
Non-patent Document 1; Yoshitomi et. al., Agricultural Machinery Society Journal, Vol. 64-3, p 101-108, 2002.

Since a tea leave processing usually involves an FA (Full Automatic) control, it is necessary to ensure that when sensing the state of tea leaves a measurement time be as short as possible, a judgment be exactly correct without being affected by shapes and characters of tea leaves, and no damage be brought to tea leaves. Further, it is considered that a method of obtaining bioelectric information can satisfy the foregoing requirements.

Plants at cell level comprise cell membranes having remarkably large resistance and electric capacity as well as small cell saps having an ionic conductivity and a small resistance. In this way, once an AC voltage is applied to plant organization organism, since a low frequency current fails to flow through the cell membranes having a large resistance but only flows through cell external saps, the plant organism as a whole has a large low-frequency impedance. On the other hand, since a high frequency current flows through cell membranes having a large electric capacity as well as through cell internal saps having a small resistance, the plant organism as a whole will have a small high-frequency impedance. Thus, an electrically uneven organism does not have constant electrical characteristics, undesirably presenting various frequency characteristics in a large range, resulting in a heterogeneous dielectric material. Further, since electrical characteristics of an electrically uneven organization organism will change remarkably depending on a frequency, it is necessary to measure frequencies in a large range to clearly find electrical characteristics of a material.

A moisture distribution of tea leaves in tea processing is usually uneven, so that the surface of each tea leave is different from its internal organization. When DC current is applied to tea leaves, electricity will not conduct into the cells of tea leaves, rendering a measurement to indicate only a moisture state of tea leave surface. On the other hand, if a high frequency AC current is applied, electricity will conduct into the cells of tea leaves, enabling a measurement to indicate a moisture state of entire tea leave organism. However, since frequency response characteristics will be different due to different items, it is necessary to select an appropriate frequency suitable for an actually processed material.

In view of the above, it is an object of the present invention to provide a method of measuring electrical characteristics of tea leaves in tea processing (drying) without having to pay attention to the shapes and the characters of tea leaves (object to be dried), and to provide a method of and an apparatus for measuring a moisture content of tea leaves with a high precision in accordance with electrical characteristics without damaging the tea leaves themselves.

In order to achieve the above-mentioned objects, the present invention is characterized by the following means and constitutions. A first invention comprises an electrode section formed of four electrodes and a device for detecting electrical characteristics changing in response to a moisture amount between electrodes. The electrode section is made of glass, an AC current for measurement is applied from one end of the electrode section to dried objects (tea leaves), thereby measuring a voltage drop of dried objects between two electrodes. At this time, since detection electrodes are connected to a high impedance voltmeter which is an LOR high tester (3532-80, manufactured by Nicchi Denki Corporation), there is almost no current flowing into measurement electrodes affected by contact resistance. In this way, there is almost no voltage drop on measurement electrodes, thereby alleviating an influence of the contact resistance. Here, the electrodes are cylindrical rod-like members which are used in the foregoing measurement by being inserted into tea leaves (dried objects) contained in a glass container, thereby allowing the electrodes to be used in measuring dried objects of any shapes.

A second invention is such that upon measuring electrical characteristics of dried objects using multiple frequencies based on the foregoing first invention, a ratio of an impedance to an electrostatic capacity shows a high correlation with a moisture content of dried objects. For example, during a rough rubbing, a medium rubbing, a fine rubbing, as well as a drying step during a tea processing, tea leaves are taken out every five minutes so that their electrical characteristics can be measured at multiple frequencies. Here, the measurement items are an impedance and an electrostatic capacity, while their ratio can be calculated by personal computer. An obtained value of the ratio shows a correlation with a moisture content measured by a dried type measuring method.

The present invention, having the above-described means and constitutions, can provide the following advantages. In all drying processes for drying objects, the present invention does not require paying attention to the shapes and characters of dried objects, thereby making it possible to measure electrical characteristics of dried objects in a stabilized manner using four electrode terminals. On the other hand, in order to effect a high precision measurement, it is necessary to correct both the electrode section and cable. By detecting electrical characteristics of the dried objects, it is possible to obtain all the information of the dried objects, thereby rendering it possible to measure other parameters of the dried objects.

A moisture content of dried objects having different characters and shapes can be expressed by a ratio of an impedance to an electrostatic capacity in all drying steps. For example, a tea processing may involve a plurality of drying steps, while a tea leave taking-out timing and a drying velocity in each step will affect the quality of coarse tea. Before now, since there was not a method capable of non-destructively and highly accurately measuring a moisture content of tea leaves, judging an appropriate tea leave taking-out timing in each step depended on a human operator's sense. In the present invention, since it is possible to quickly measure a tea leave taking-out timing and a drying velocity which are the most important parameters in tea processing, it is possible to control these parameters in each step without depending on a human operator's judgment. Therefore, the present invention provides a technique capable of quickly satisfying an FA control used in a tea leave workshop.

BRIEF DESCRIPTION OF THE DRAWINGS

Next, description will be given to explain in detail an optimum embodiment for carrying out the present invention based on a tea processing, with reference to the accompanying drawings.

Referring to FIGS. 1 and 2, an electrode section 3 for non-destructively measuring a moisture content of tea leaves according to the present invention comprises a disk-like fixing base 3a consisting of an easily workable silicon rubber and having a predetermined thickness, and four electrode terminals 3b made of a highly durable stainless steel and fixed through the disk-like fixing base 3a, with a predetermined interval among one another on the front side of the base 3a and terminals 3c protruding from the backside thereof. The electrode terminals 3b are rod-like members each having a diameter of 3.0 mm and a length of 4.5 cm, and separated from one another at an interval of 7.0 mm. Each electrode 3b is fixed on the fixing base 3a and coated with silicon (TSK550 manufactured by GE Toshiba Silicon Corporation) so as to form an exact insulation among the electrode terminals 3a. In this way, the electrode terminals 3a are so formed that an AC signal for measurement can be applied to the dried objects (tea leaves) to measure a voltage drop of the dried objects between two terminals. At this time, since the electrodes are connected to LCR high tester 2 (3632-80 manufactured by Nicchi Denki Corporation) which is a high impedance voltmeter, there is almost no electric current flowing into measurement electrodes affected by contact resistance. In this way, there is almost no voltage drop on measurement electrodes, thus rendering it possible to reduce an influence of contact resistance. Here, although the electrodes of the electrode section 3 are all in a cylindrical rod-like shape, they are also possible to be formed in other shapes. Besides since the present invention adopts a measuring method in which electrode terminals 3b are inserted in dried objects, such electrode terminals are suitable for measuring dried objects of any shapes. When the electrical characteristics of the dried objects are measured at multiple frequencies, a ratio of an impedance to an electrostatic capacity will show a high correlation with a moisture content of the dried objects. During a rough rubbing, a medium rubbing, a fine rubbing as well as a drying step during a tea processing, tea leaves are taken out every five minutes so that their electrical characteristics can be measured at multiple frequencies. Here, the measurement items are an impedance and an electrostatic capacity, while their ratio can be calculated by personal computer. An obtained value of the ratio shows a correlation with a moisture content measured by a dried type measuring method.

FIG. 2 shows a measuring system (apparatus) for measuring electrical characteristics of tea leaves. In FIG. 2, sign 1 represents a personal computer connected with LCR high tester 2 (3532-80 manufactured by Nicchi Denki Corporation) which is a high impedance voltmeter. The electrode section 3 is covered by a connecting cap 2a connected with each connecting terminal 3c through a lead wire 2b. A cable 2c collecting the respective lead wires 2b is connected to the LCR high tester 2. The tea leaves, a moisture content of which is to be measured, are received into a cylindrical glass container 3d having a capacity of 42 mm3, while the electrode terminals 3b of the electrode section 3 are inserted into the dried objects so as to measure their moisture content. Here, an AC current having a frequency of 10 Hz to 1.0 MHz is applied to the electrode terminals 3b to measure an impedance and an electrostatic capacity of tea leaves by the LOR high tester 2. Since air can be detected as condenser when an AC current has a high frequency of 1.0 MHz or more, an AC current to be applied is required to have a frequency which is not higher than 1.0 MHz.

Figure 1:
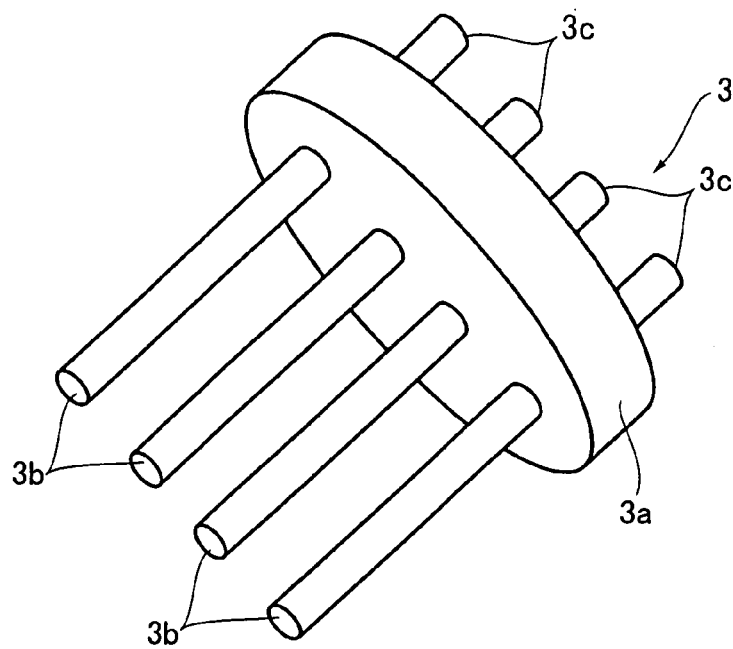
FIG. 1 is a perspective view showing an electrode section according to the present invention.
Figure 2:
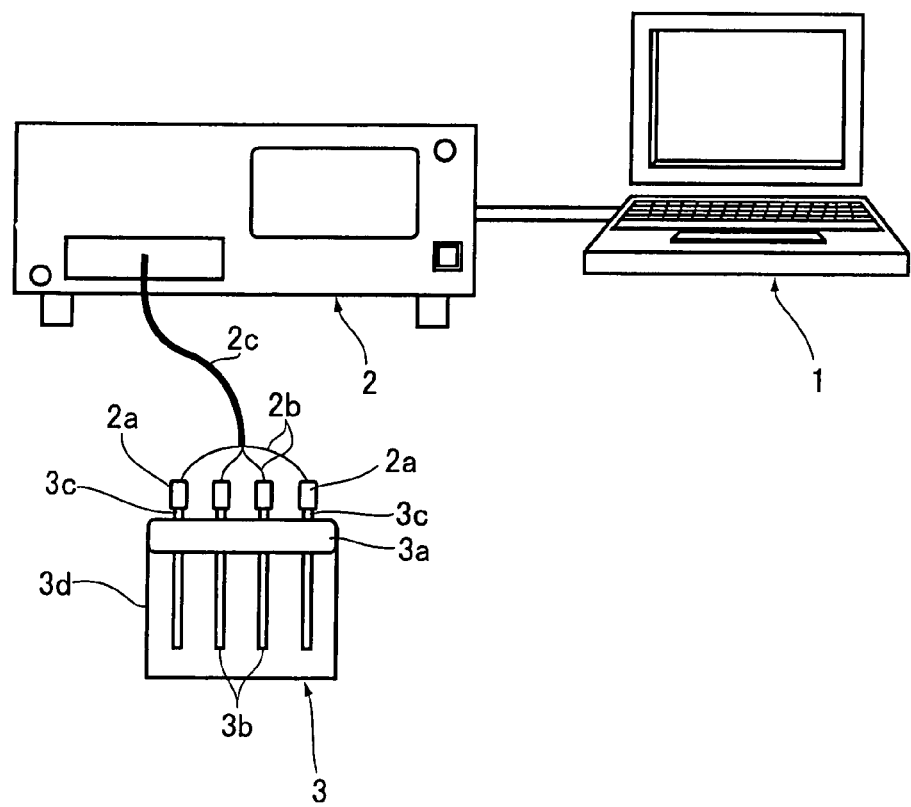
FIG. 2 is a front view showing a system (apparatus) and the electrode section according to the present invention for measuring electrical characteristics of dried objects.

Before measuring the impedance and electrostatic capacity of tea leaves by the electrode section 3, the electrode terminals 3b and the cable 2C are corrected. There are two kinds of corrections, one of which is to correct a floating admittance of the cable 2c connecting the electrode terminals 3b to the LCR high tester 2, while the other of which is to correct a remaining impedance. By performing these corrections, it is possible to increase a measurement precision and to measure specimens from those having a high impedance to those having a low impedance. The values of the measured impedance and electrostatic capacity are inputted into the personal computer 1 through the LCR high tester 2 and calculated therein. However, a time for measuring one sample is set at one minute.

Figure 3:
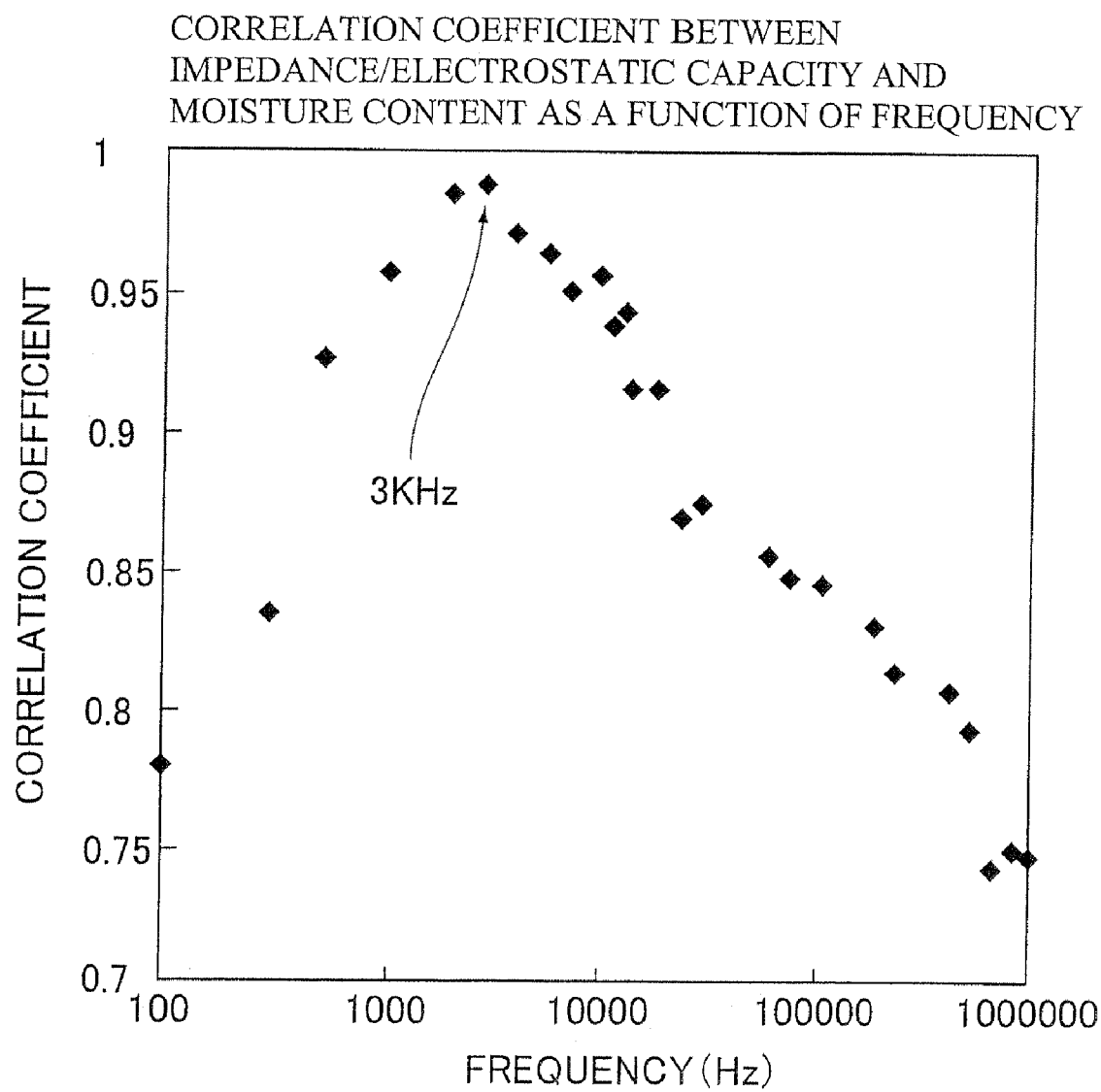
FIG. 3 is a graph showing a relation between impedance/electrostatic capacity and moisture content of tea leaves at different frequencies, according to the present invention.

The variety of raw leaves to be processed in the present embodiment is "Yabukita". The raw leaves are at first steamed for 60 seconds and then introduced into each rubbing/drying step. The tea leaves are processed in each rubbing/drying step and taken out every five minutes, thereby measuring the impedance and electrostatic capacity of tea leaves at various frequencies using the foregoing means, and calculating their ratio in the personal computer 1. Soon after that, a moisture content of the tea leaves is measured using a dried type measuring method, while the values of the ratios and the moisture contents measured by the dried type measuring method are processed statistically, thereby selecting a frequency having a highest correlation with moisture content. FIG. 3 shows a relation between impedance/electrostatic capacity at various frequencies on one hand and a moisture content on the other. As can be clearly seen in FIG. 3, when a frequency begins to increase, a correlation coefficient becomes close to 1, with a highest correlation of 0.99 being obtained at a frequency of 3.0 kHz. On the other hand, it can be clearly seen in FIG. 3 that when a frequency is larger than 3.0 kHz, the correlation coefficient becomes smaller than 1. Therefore, it is understood that an impedance and an electrostatic capacity within a high frequency band will receive some other influences than a moisture content of tea leaves.

Figure 4:
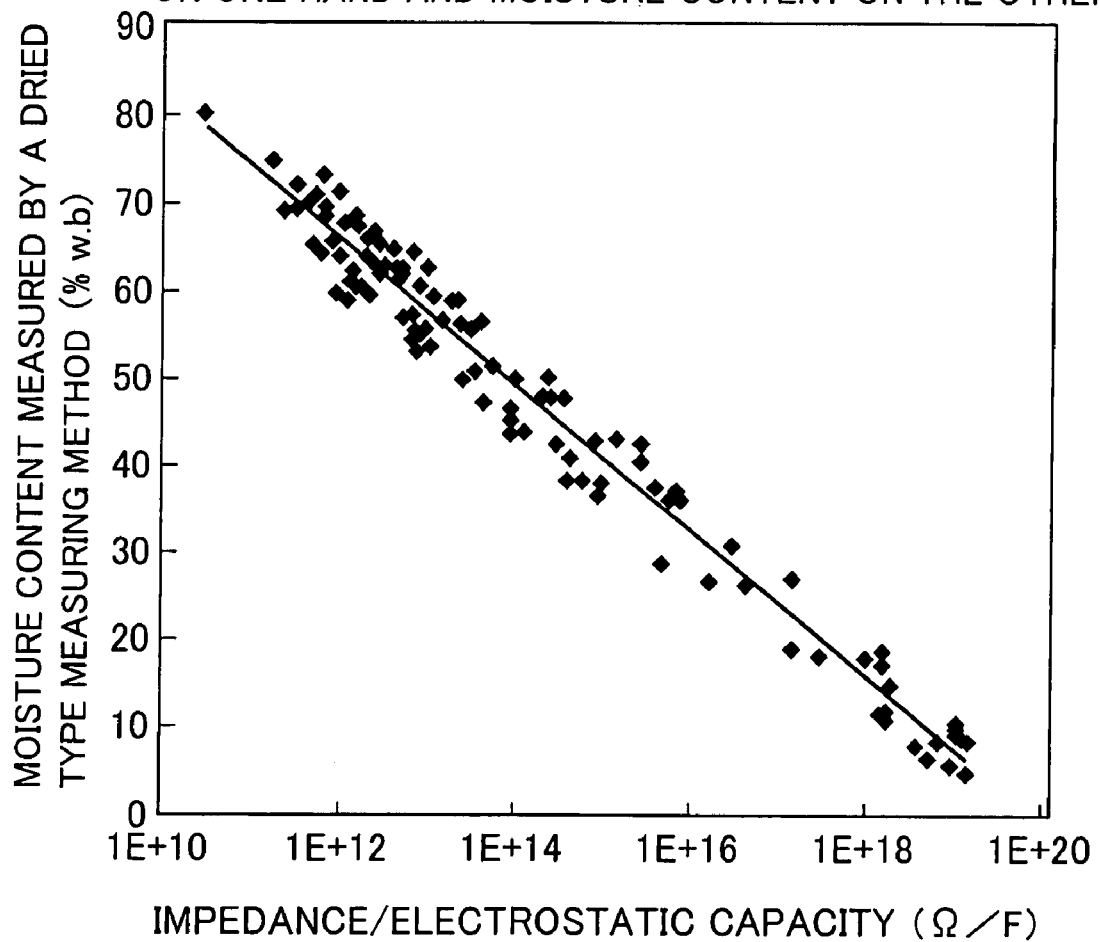
FIG. 4 is a graph showing a relation between impedance/electrostatic capacity of tea leaves measured according to the present invention when applying an AC current having a frequency of 3.0 kHz on one hand and a moisture content of tea leaves measured by a dried type measuring method on the other.

FIG. 4 shows a relation between an impedance/electrostatic capacity and a moisture content of tea leaves when an AC current having a frequency of 3.0 kHz is applied to the electrode terminals 3b of the electrode section 3. In fact, this relation can be approximated by an exponential function. In practice, an impedance/electrostatic capacity and a moisture content of tea leaves can be represented as follows.

$$\omega W = -3.65 \ln(Z/Cp) + 166.77 \quad \text{[Equation 1]}$$

In the above equation, $\omega W$ represents a moisture content of tea leaves which satisfies a moist criteria, Z represents an impedance ($\Omega$) of tea leaves at a frequency of 3.0 kHz, Cp represents an electrostatic capacity (F).

Figure 5:
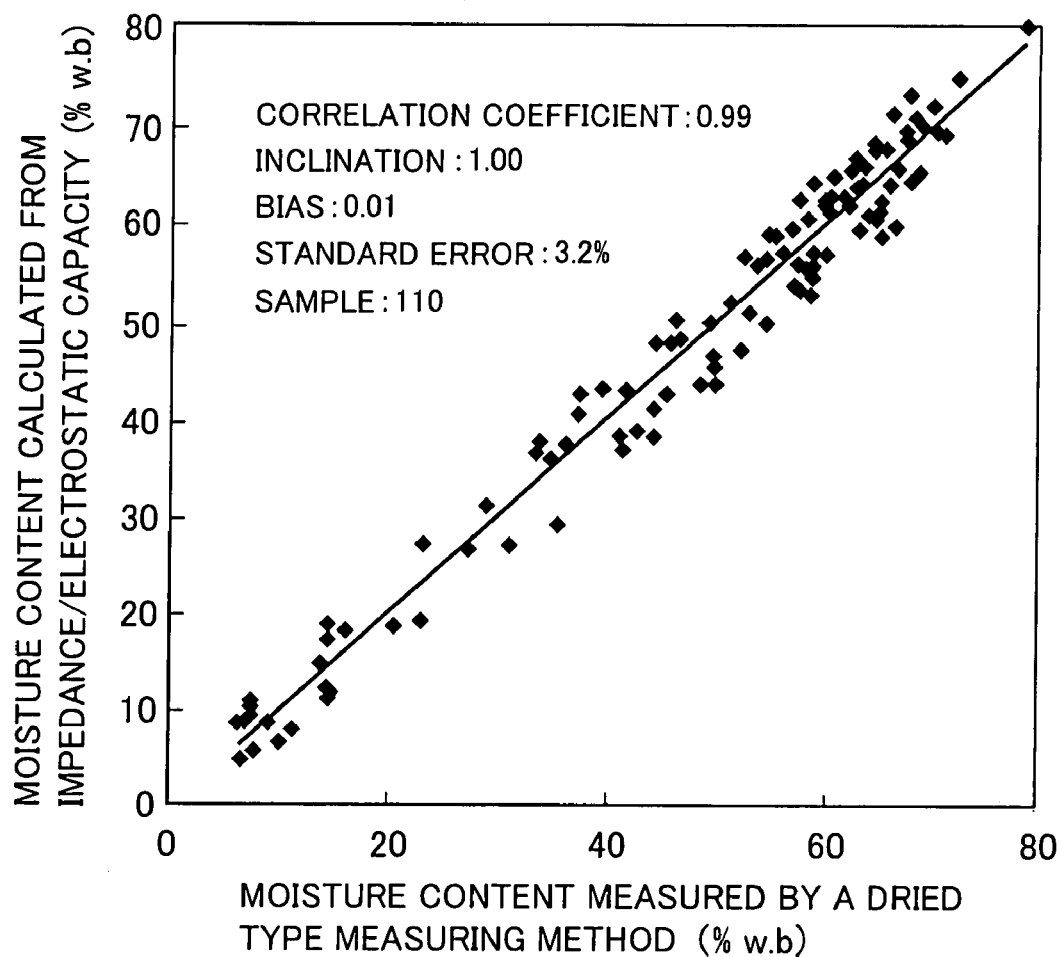
FIG. 5 is a graph showing a relation between a moisture content calculated from impedance/electrostatic capacity of tea leaves measured according to the present invention when applying an AC current having a frequency of 3.0 kHz on one hand and a moisture content of tea leaves measured by a dried type measuring method on the other.

FIG. 5 shows a relation between a moisture content calculated from the measured impedance/electrostatic capacity at a frequency of 3.0 kHz on one hand and a moisture content measured by a dried type measuring method on the other. As shown, a moisture content of tea leaves is 6.0% to 8.0%, a correlation coefficient is 0.99, an inclination of a straight line is 1.00, a bias is 0.01%, a standard error is 3.2%. On the other hand, an upper confidence limit is 1.6% and a lower confidence limit is also 1.6%. In this way, it is clear that an impedance/electrostatic capacity at a frequency of 3.0 kHz can well express a moisture content of tea leaves. However, when the impedance and electrostatic capacity at a frequency of 3.0 kHz are measured, the measuring time is set within 1.0 second.

Nevertheless, the non-destructive moisture content measuring method and apparatus of the present invention should not be limited to the moisture content measurement in the tea processing of the present embodiment. In fact, when artificially drying agricultural products such as cereals, fruits, marine products or the like, it is also possible to use the method and apparatus of the present invention to measure a change in the moisture content of dried objects so as to put the dried objects in an appropriate dried state.

INDUSTRIAL APPLICABILITY

The non-destructive moisture content measuring method and apparatus of the present invention can be used in a drying step to measure a moisture content of dried objects with a high precision but without damaging the dried objects themselves. Therefore, the present invention can contribute to an improvement of a sensing technique which is the most important in FA control used in a drying process. This means that the present invention can contribute to the development of an artificial drying technique in which a full automation is anticipated in the future. When carrying out an artificial drying of dried objects, it is very important to quickly measure a moisture content of dried objects so as to judge a timing for taking out the dried objects during a drying process. In tea processing, a rough rubbing step for drying tea leaves to reduce its moisture content from 80% (dw) to 50% (dw) will greatly affect a tea processing quality, but it was proved difficult to non-destructively measure a moisture content of dried objects having a high moisture content. This problem however has been solved by the present invention. By measuring an impedance and an electrostatic capacity, it becomes possible to measure a moisture content of tea leaves having a moisture content of 6.0% (dw) to 80% (dw). Besides, since the apparatus of the present invention does not have a complex structure, it can be used in tea processing industry at an extremely high applicability.

EXPLANATION OF REFERENCE NUMERALS

1 personal computer for data analysis
2 LCR high tester
2a connecting cap
2b lead-wire
2c cable
3 electrode section
3a electrode fixing base
3b electrode Terminals
3c connecting terminals
3d glass container

The invention claimed is:

1. A method of non-destructively measuring a moisture content of dried objects, said method comprising the steps of:
   introducing dried objects during a drying process into containers having different shapes and sizes;
   inserting four electrode terminals into the containers;
   applying an AC signal having a predetermined voltage to the electrode terminals;
   measuring electrical characteristics between two electrodes based on the dried objects and inputting measurement results into a high impedance voltmeter; and
   non-destructively measuring the moisture content of the dried objects, characterized in that:
   the moisture content of the dried objects is represented by calculating a ratio of an impedance to an electrostatic capacity,
   wherein a ratio of an impedance to an electrostatic capacity at a frequency of 3.0 kHz represents a moisture content of tea leaves during a tea processing.

* * * * *